United States Patent [19]

Weidler et al.

[11] Patent Number: 5,502,043
[45] Date of Patent: Mar. 26, 1996

[54] USE OF HYDROXYETHYL STARCH FOR IMPROVEMENT OF MICROCIRCULATION

[75] Inventors: Burghard Weidler; Klaus Sommermeyer, both of Rosbach; Klaus Henning, Usingen; Frank Bepperling, Rosbach, all of Germany

[73] Assignee: Fresenius AG, Bad Homburg, Germany

[21] Appl. No.: 220,150

[22] Filed: Mar. 30, 1994

[30] Foreign Application Priority Data

Apr. 3, 1993 [DE] Germany .............. 43 10 974.8

[51] Int. Cl.$^6$ .............. A61K 31/72; A61K 31/70; C08B 31/10
[52] U.S. Cl. .............. 514/60; 514/832; 514/833; 536/111
[58] Field of Search .............. 514/60, 832, 833; 536/111

[56] References Cited

FOREIGN PATENT DOCUMENTS

| 0402724 | 6/1990 | European Pat. Off. . |
|---|---|---|
| 3030863A1 | 3/1982 | Germany . |
| 3030863 | 3/1982 | Germany . |
| 4023789 | 1/1992 | Germany . |

OTHER PUBLICATIONS

Infusionstherapie, Bd. 17, Nr. 2, 1990 Seiten 79—82, Kortsik, C. F. et al. "Konjunktivaler Sauerstoffpartialdruk, Hamorheologie Und Krieslaufparameter Bei Akutem Zerebralem Insult Vor Und Nach Infusion Von 6Prozentiger Niedermolkularer Hydroxyathylstarke".

Arzneimittelforschung, Bd. 43(10, Nr. 2, 1993 Seiten 99—105, Jung, F. et al. "Einfluss Der Molekulstruktur Von Hydroxyathylstarke Aug Die Eliminationskinetik Und Die Fliessfahigkeit Des Blutes Bei Probanden".

Arzneimittelforschung, Bd. 41, Nr. 5, 1991 Seiten 494—498 Weidler, B. et al. "Pharmakinetische Merkmale Als Kriterien Fur Den Klinischen Einsatz Von Hydroxyathylstarke".

Lutz, H. and Hartung, H. J., "State of Investigations on Hydroxyethylstarch".

Ehrly, A. M. et al., "Verbesserung der FlieBeigenschaften des Blutes nach Infusion von niedermolekularer Hydroxyäthylstäke (Expafusin©) bei gesunden Probanden", *Infusiontherapie*, 6:331–336 (1979).

Primary Examiner—Ronald W. Griffin
Attorney, Agent, or Firm—Robbins, Berliner & Carson

[57] ABSTRACT

The use of a hydroxyethyl starch specification with a molecular weight $M_W$ of 110,000 to 150,000, a substitution level MS of 0.38 to 0.5, a substitution level DS of 0.32 to 0.45, and a $C_2/C_6$ ratio from 8 to 20 for improvement of microcirculation in a peripheral arterial circulation disorder, in particular in already existing peripheral arterial occlusive disease in Stage II according to Fontaine. This hydroxyethyl starch specification can be used in suitable concentrations, e.g., as 6 wt.-% or 10 wt.-% solution, whereby these solutions optionally contain conventional adjuvants and additives.

4 Claims, 9 Drawing Sheets

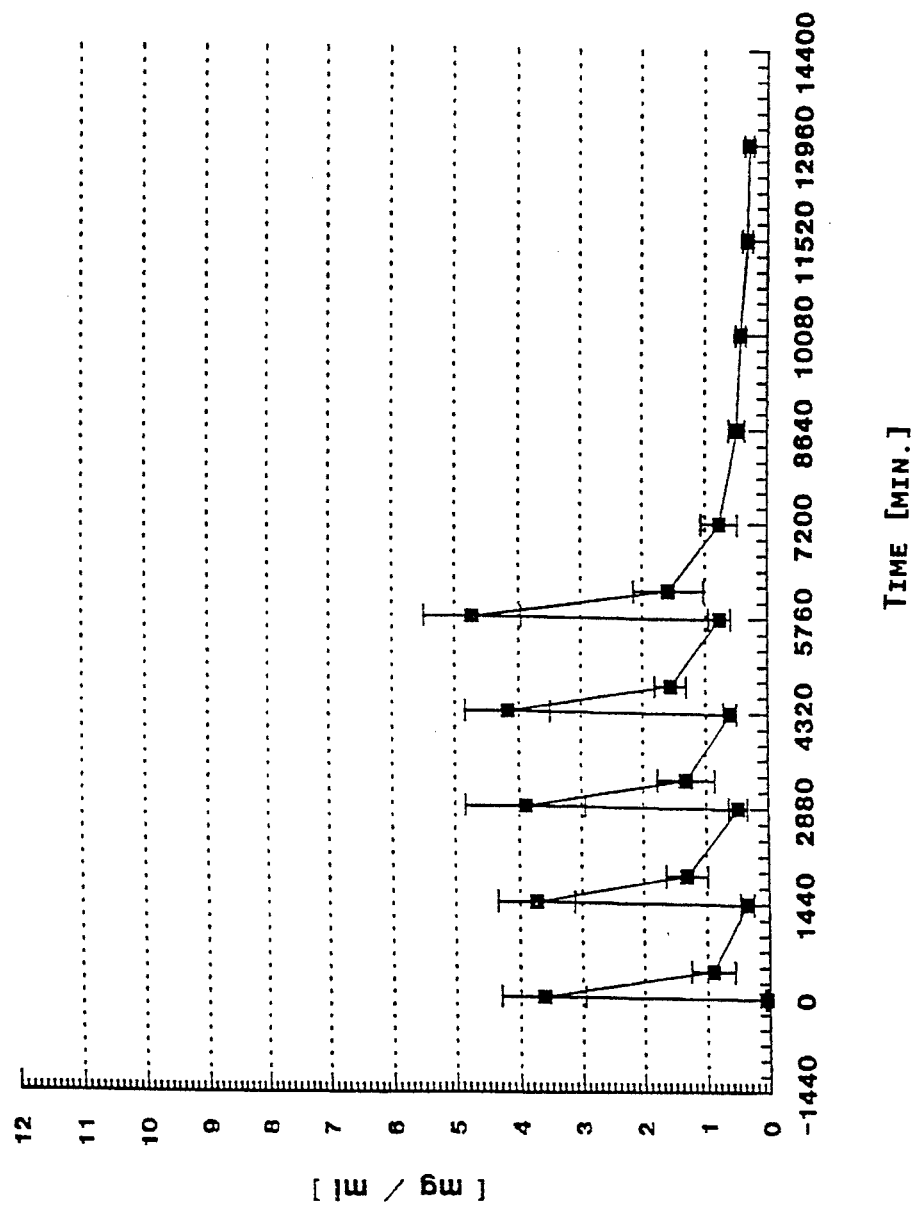

USE OF HYDROXYETHYL STARCH FOR IMPROVEMENT OF MICROCIRCULATION

BACKGROUND OF THE INVENTION

The present invention relates generally to the medical arts.

Arterial circulation disorders, such as peripheral arterial occlusive disease, acute cerebral insult, ocular infarct, hearing loss, placental circulation disorders, etc., are among frequently occurring diseases, which sometimes require extremely lengthy treatment (with varied success) and present significant impairment.

Hydroxyethyl starch (HES) has already been used within the framework of hemodilution therapy in patients with arterial circulation disorders. The therapeutic principle in hemodilution is the rheologic improvement of the blood, such as lowering the hematocrit, reducing plasma viscosity, as well as normalizing erythrocyte aggregation. Hematocrit, plasma viscosity, and erythrocyte aggregation are rheologic parameters whose value provides indications concerning the fluidity of the blood [see Kiesewetter, VASOMED, Vol. 4, 10/92, pp. 672–686].

In clinical studies the principle of action was confirmed, whereby the clinical relevance of improved rheology, for example, in peripheral arterial occlusive disease was demonstrated in an increase in pain-free walking distance or in acute cerebral infarct in an improvement in neurological scores.

Currently, commercial medium-molecular hydroxyethyl starch, such as HES 200/0.60 to 0.66 and HES 200/0.5 are used in hemodilution therapy for circulation disorders. In hemodilution therapy with HES solutions, large quantities of these solutions are infused, e.g., as much as 10 l of a 10% HES solution within a period of 10 days with acute cerebral infarct and up to 42 days with peripheral arterial occlusive disease, which corresponds to an infused quantity of 1 kg of HES. In examinations, it has been determined that multiple infusions of HES solutions resulted in cumulation of the serum HES concentrations. Thus, for example, with repeated administration of HES 450/0.7 (2×weekly 500 ml 6% HES solution over a period of 6 weeks) serum concentrations around 20 g/l were obtained, and 16 weeks after this repeated administration HES concentrations of approximately 1.32 g/l were still found [FORTSCHRITTE DER MEDIZIN Vol. 97, No. 40 (1979), pp. 1809–1813].

Furthermore, with the infusion of the prior art HES solutions, because of the cumulation of the serum HES concentrations, adverse effects, such as allergic reactions (e.g., pruritus, etc.), were observed. To avoid such adverse effects, specialists recommended that in therapy with HES patients be infused with no more than 150 g hydroxyethyl starch, which corresponds to 3×500 ml HES 200/0.5 (10%) or 5×500 ml HES 200/0.5 (6%) per week [J. Koscielny, H. Kiesewetter, et al., Hemodilution, Springer Verlag, 1991, p. 214].

For microcirculation, improvement of which is an essential principle or the most essential principle in the therapy of peripheral circulation disorders, plasma viscosity is an important criterion along with hematocrit and erythrocyte aggregation. Whereas previously used HES solutions lower the hematocrit value and improve erythrocyte aggregation, their effect on the lowering of plasma viscosity to bring about a significant improvement of microcirculation was inadequate. Thus, for the treatment of peripheral arterial occlusive diseases, HES is often combined with vasoactive substances.

With regard to these disadvantages, there continues to be a need for suitable agents for improvement of microcirculation in peripheral circulation disorders, such as peripheral arterial occlusive diseases, which do not have the disadvantages of the prior art agents.

The object of the present invention is thus to provide an agent for improvement of microcirculation in peripheral circulation disorders, in particular in peripheral arterial occlusive diseases in Stage II according to Fontaine, with which microcirculation can be substantially improved, even without the addition of vasoactive substances.

SUMMARY OF THE INVENTION

In accordance with the present invention, use is made of a hydroxyethyl starch with a molecular weight $M_W$ of 110,000 to 150,000, a substitution level MS [molar substitution] of 0.38 to 0.5, a substitution level DS [degree of substitution] of 0.32 to 0.45, and a $C_2/C_6$ ratio from 8 to 20 for improvement of microcirculation in already existing peripheral arterial occlusive disease in Stage II according to Fontaine.

BRIEF DESCRIPTION OF THE DRAWINGS

The invention may be better understood with reference to the accompanying drawings, in which:

FIG. 9 shows serum HES concentration in patients infused on 5 consecutive days in each case with 500 ml of a 6 wt.-% solution of HES 130/0.5 within 30 minutes over the examination period of 10 days.

DETAILED DESCRIPTION OF THE INVENTION

Figure 1:
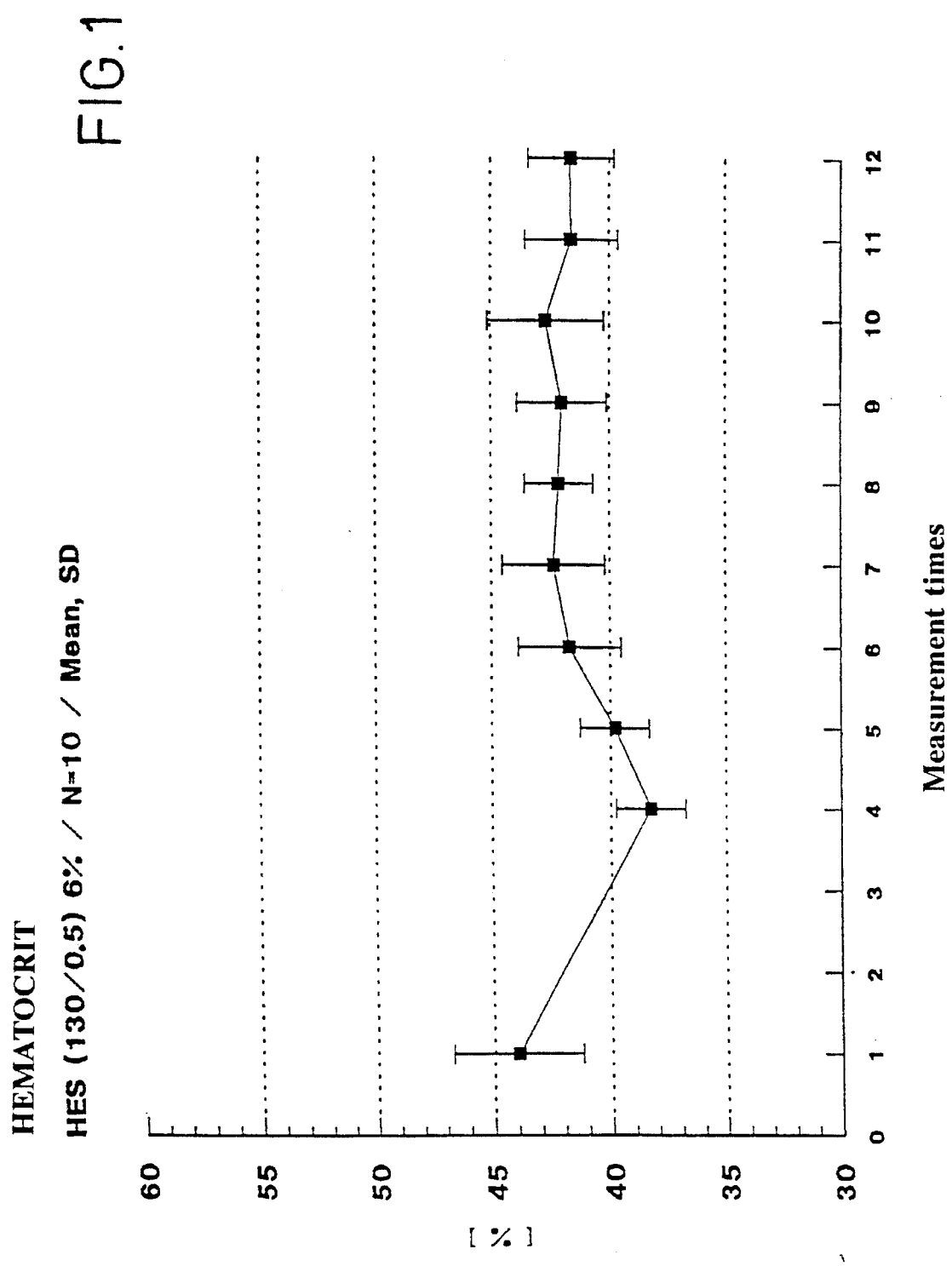
FIG. 1 shows the course of the hematocrit for patients intravenously infused one time with 500 ml of a 6 wt.-% solution of HES 130/0.5 during the examination period.

According to the invention, it was unexpectedly discovered that with an HES specification with a molecular weight $M_W$ of 110,000 to 150,000, a substitution level MS [molar substitution] of 0.38 to 0.5, preferably from 0.38 to 0.45, a substitution level DS [degree of substitution] of 0.32 to 0.45, preferably from 0.32 to 0.42, and a $C_2/C_6$ ratio from 8 to 20, a significant improvement of plasma viscosity is obtained and thus an improvement of microcirculation can be effected in peripheral circulation disorders, in particular in peripheral arterial occlusive disease in Stage II according to Fontaine.

As a result of the use of the natural raw starting material amylopectin, as well as of the production process, in which a splitting of the polymer chains is necessary to a certain extent, hydroxyethyl starch is available not as a molecularly uniform substance with a defined molecular weight, but rather as a mixture of molecules of different sizes, which are also substituted differently by hydroxyethyl groups. The characterization of such mixtures requires the help of statistically determined values. To identify the average molecular weight, the averaged molecular weight $M_W$ is used, with the general definition of this average value reported in KRANKENHAUSPHARMAZIE [Hospital Pharmacy] (1987), pp. 271 et seq.

There are two differently defined substitution levels to determine the substitution by hydroxyethyl groups. The substitution level MS (molar substitution) is defined as the average number of hydroxyethyl groups per anhydroglucose unit. It is determined from the total number of hydroxyethyl groups in a sample, for example, according to Morgan's method, by ether splitting and subsequent quantitative determination of ethyl iodide and ethylene formed in the process. The substitution level DS (degree of substitution) is defined as the share of substituted anhydroglucose units of all anhydroglucose units. It can be determined from the quantity of unsubstituted glucose measured after hydrolysis of a sample.

The ratio of the substitution of $C_2/C_6$ means the ratio of the number of anhydroglucose units substituted in the No. 2 position to the number of anhydroglucose units substituted in the No. 6 position of the hydroxyethyl starch.

The infusion of the HES specification according to the invention results in a significant reduction in plasma viscosity already immediately after the end of the infusion, a significant lowering of hematocrit, as well as a significant reduction of erythrocyte aggregation.

Through these rheologic changes in the blood, a significant improvement of microcirculation is obtained in peripheral circulation disorders, for example, in peripheral arterial occlusive disease in Stage II according to Fontaine. The rheologic properties of the blood are unexpectedly altered by the HES specification according to the invention, and to a greater extent than is possible with the prior art hydroxyethyl starch used for hemodilution therapy. Thus, plasma viscosity is significantly altered by the HES specification used according to the invention compared to hydroxyethyl starch 200/0.5 and hydroxyethyl starch 200/0.3. After infusion of the HES specification according to the invention, plasma viscosity dropped toward the end of the investigation whereas under comparable conditions after infusion of HES 200/0.5 and 200/0.3, plasma viscosity clearly increased toward the end of the investigation. Compared to HES 200/0.5, the hydroxyethyl starch most used in medicine for hemodilution therapy, with the HES specification used according to the invention plasma viscosity clearly dropped already toward the end of the infusion and with the HES specification used according to the invention plasma viscosity was significantly lowered in the temporal course.

Also, after multiple doses with the HES specification used according to the invention, plasma viscosity was positively affected.

Furthermore, it was unexpectedly found that the serum elimination of the HES specification used according to the invention is very good after a one-time infusion. In particular, after multiple infusion of the HES specification used according to the invention, no cumulation (less than 1 mg/ml) of HES concentrations in the serum was observed. In the remaining residual serum HES fraction the average molecular weight $M_W$ was 70 kda. This corresponds to the renal threshold for elimination of hydroxyethyl starch.

The HES specification used according to the invention is produced in the conventional manner, as described, for example, in the German Offenlegungsschrift 39 19 729, to which publication full reference is made.

The administration of the HES specification used according to the invention takes place in the form of aqueous solutions in which the HES is present in conventional concentrations. Concentrations in the range from 5 to 15 wt.-%, preferably 6 to 10 wt.-%, are suitable. Suitable concentrations are, for example, the 6 wt.-% concentration and the 10 wt.-% concentration, with the 6 wt.-% concentration preferred. These solutions may contain conventional adjuvants and additives.

The rheologic changes in the blood effected after infusion of the HES specification used according to the invention with rapid serum elimination without the risk of cumulation of high molecular residual serum HES fractions, even with multiple use, assure an effective and safe use of the HES specification used according to the invention over a relatively long period in patients with arterial circulation disorders, in particular in peripheral arterial occlusive disease in Stage II according to Fontaine.

The following examples serve to illustrate the present invention.

EXAMPLE 1

In a study, 10 healthy male subjects were intravenously infused one time with 500 ml of a 6 wt.-% solution of HES 130/0.5, i.e., HES with a $M_W$ of 136,800, MS of 0.396, DS of 0.346, and a $C_2/C_6$ ratio of 10.8 within 30 minutes. The examination period was 72 hours. Within this period, hematocrit, plasma viscosity, and erythrocyte aggregation of the blood were determined at specified measurement times. The examination results can be seen in FIGS. 1 through 3.

FIG. 1 shows the course of the hematocrit during the examination period. The hematocrit dropped at the end of infusion (measurement time 4) by 15% and also remained 6% below the starting value 3 days after the infusion. The p-value in the temporal course is p<0.001.

Figure 2:
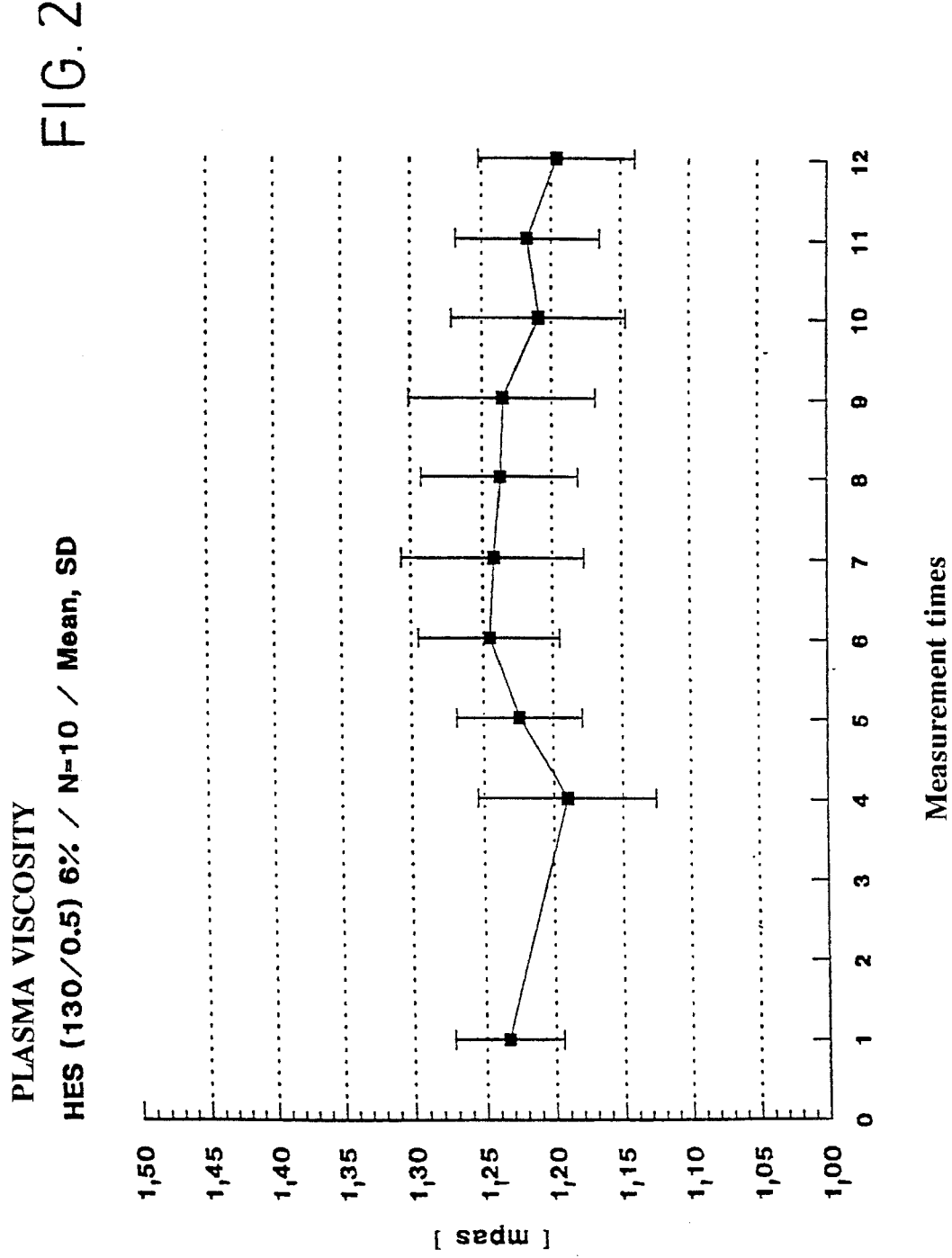
FIG. 2 shows the course of the plasma viscosity in the patients described in connection with FIG. 1.

FIG. 2 shows the course of the plasma viscosity. Already immediately after the end of the infusion (measurement time 4), the plasma viscosity was lowered by 4% and after one hour (measurement time 5) it was again at its starting level. The p-value in the temporal course is p<0.05.

Figure 3:
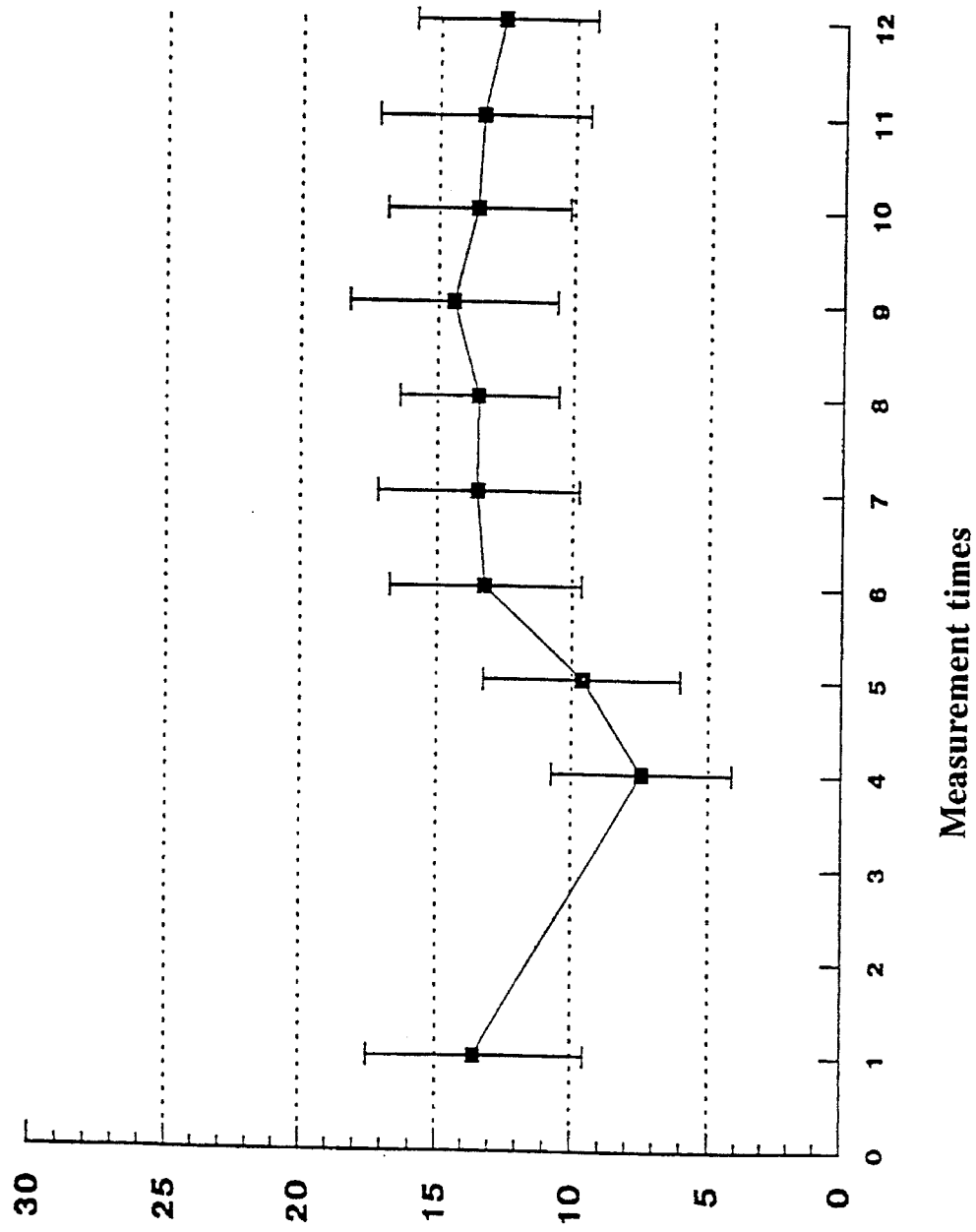
FIG. 3 shows the course of the erythrocyte aggregation in the patients described in connection with FIG. 1.

FIG. 3 shows the course of the erythrocyte aggregation. At the end of the infusion (measurement time 4) the erythrocyte aggregation was virtually halved; however, after 2 hours it again reached its starting level. The p-value in the temporal course is p<0.001.

The values found demonstrate a pronounced hematocrit-reducing action as well as a very pronounced erythrocyte aggregation-reducing action. Particularly noteworthy is the lowering of plasma viscosity already after the end of the infusion caused by the HES 130/0.5 solution used according to the invention.

EXAMPLE 2

Figure 4:
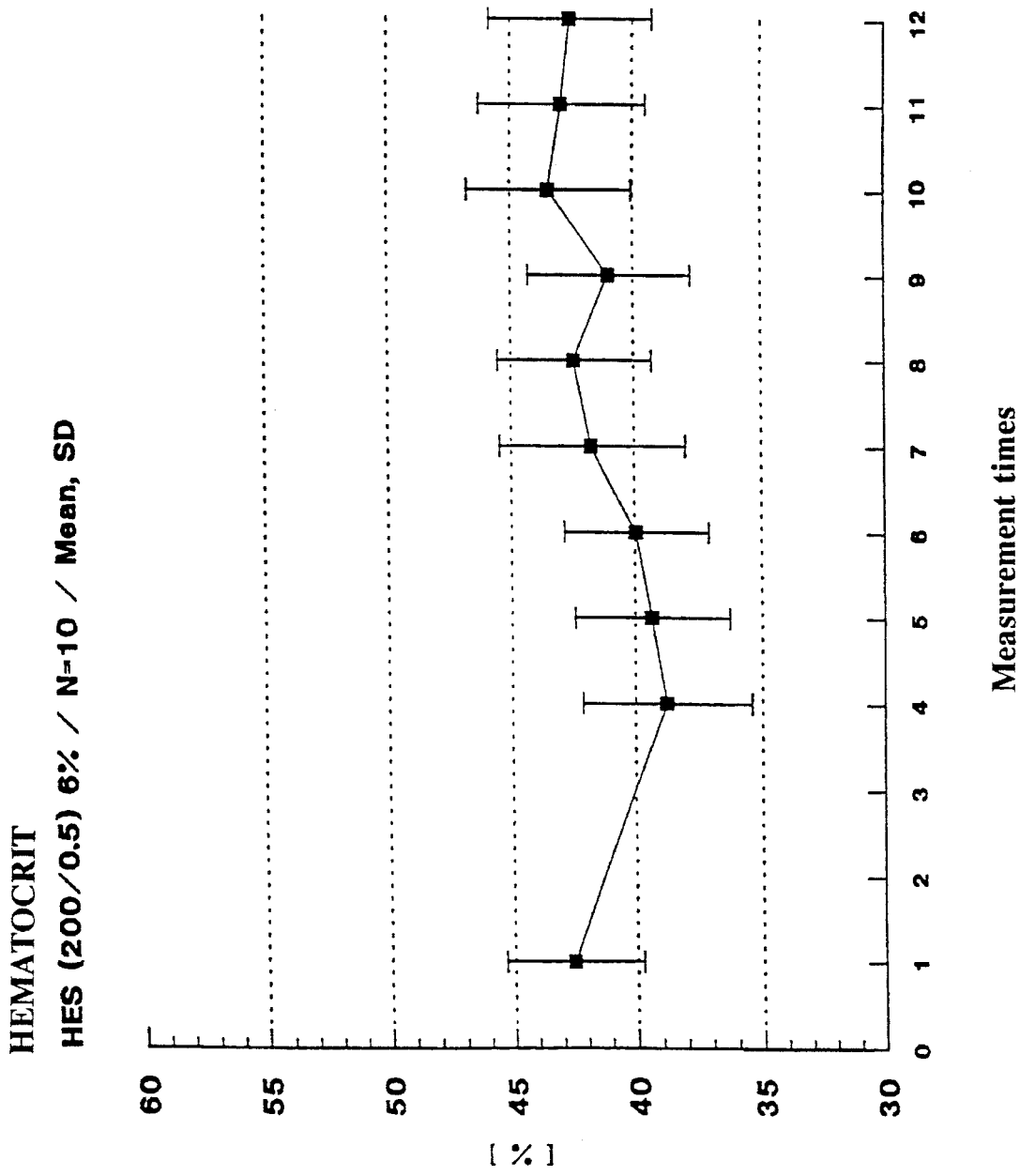
FIG. 4 shows the hematocrit values for patients intravenously infused one time with 500 ml of a 6 wt.-% solution of HES 200/0.5 within 30 minutes.
Figure 5:
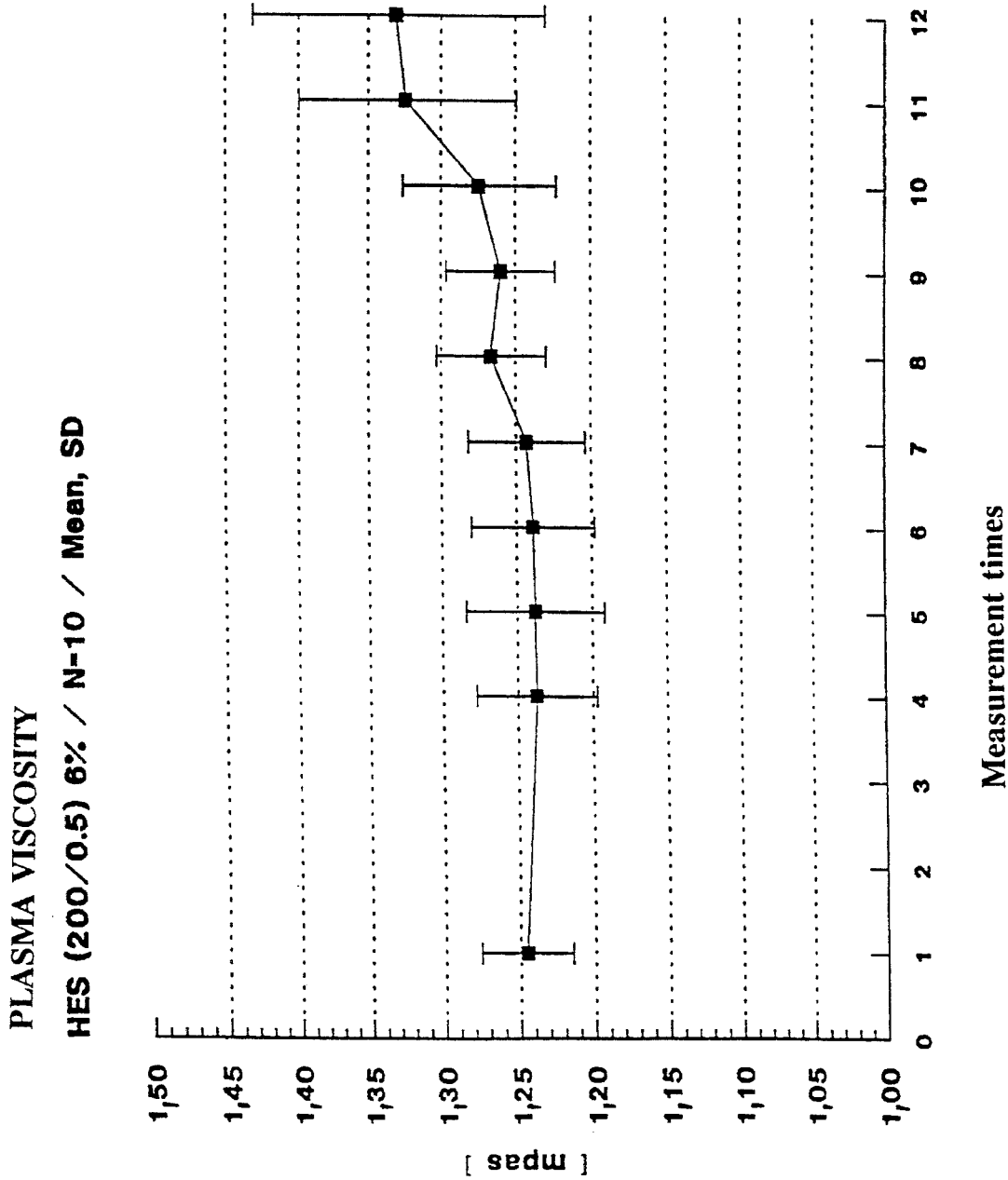
FIG. 5 shows the plasma viscosity values for the patients described in connection with FIG. 4.

For comparison, 10 healthy male subjects were intravenously infused, under the same conditions as described above in Example 1, one time with 500 ml of a 6 wt.-% solution of HES 200/0.5 within 30 minutes. The examination period was 72 hours. Within this period, hematocrit and plasma viscosity were determined at specific measurement times, which coincided with the measurement times according to Example 1. The results obtained can be seen in FIGS. 4 and 5.

Figure 6:
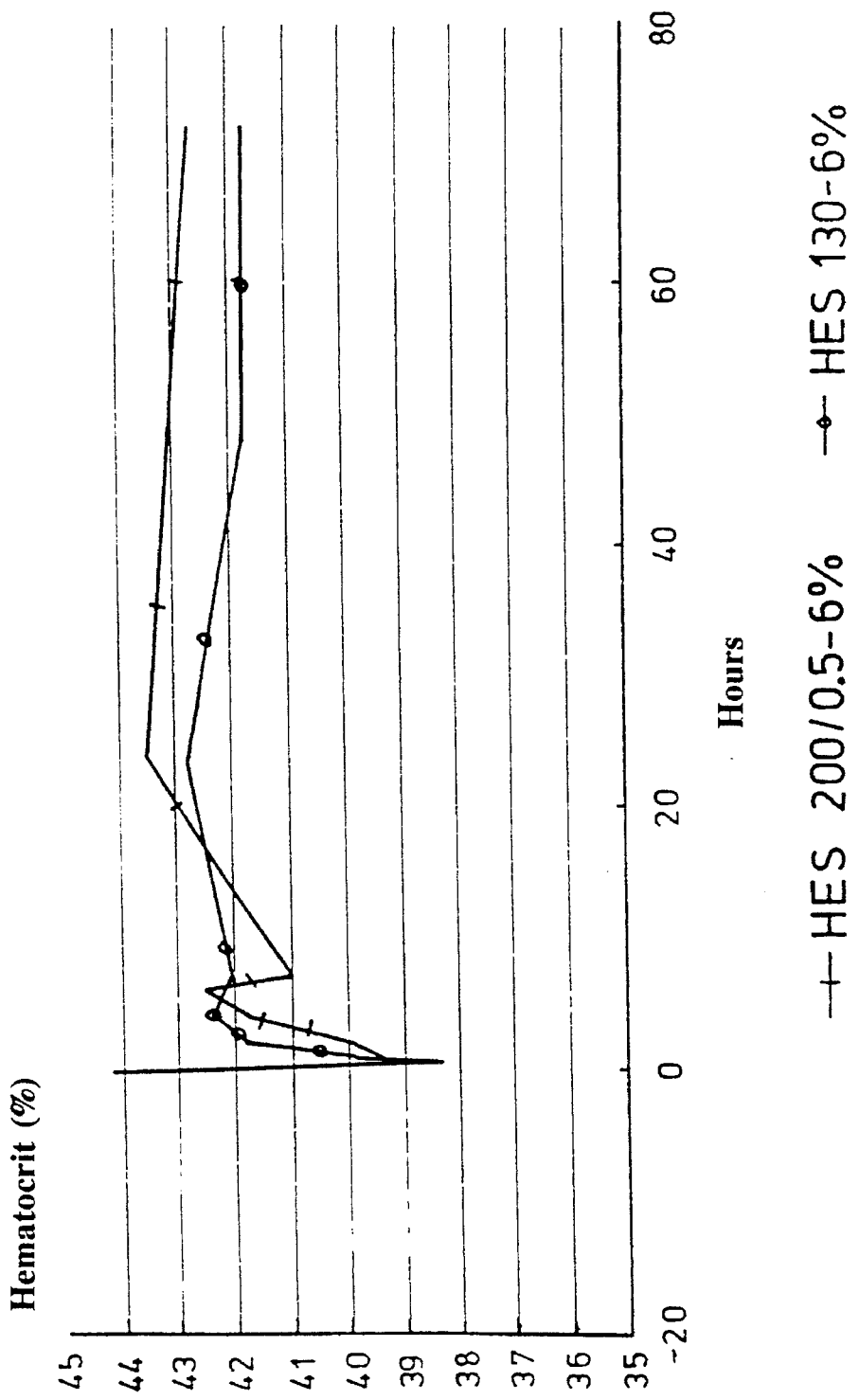
FIG. 6 shows lowering of the hematocrit with HES 130/0.5 and HES 200/0.5 treatment.
Figure 7:
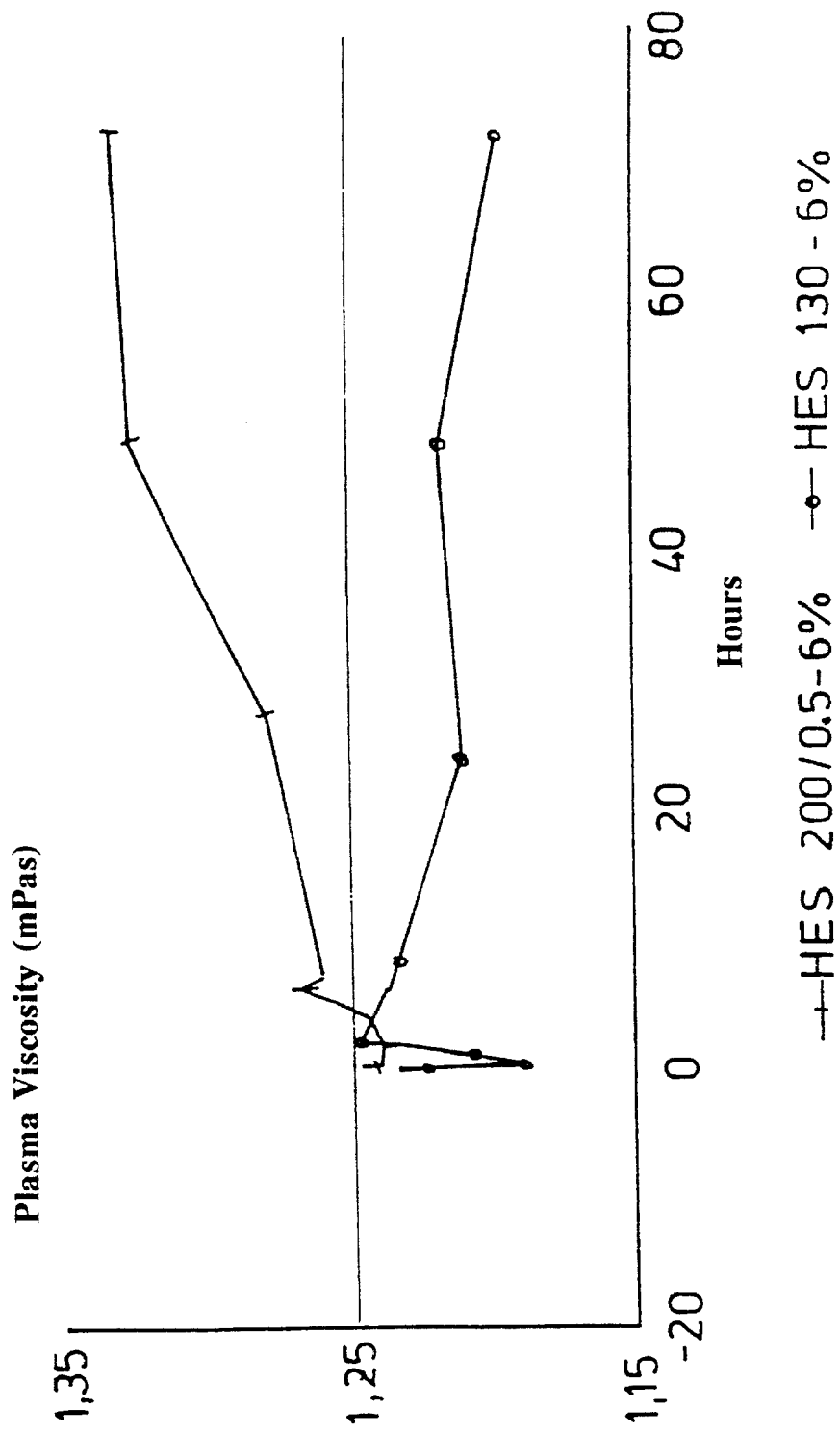
FIG. 7 shows the plasma viscosity following treatment with HES 130/0.5 and HES 200/0.5.

The examination results, as obtained above in Examples 1 and 2, were juxtaposed for better comparison in FIGS. 6 and 7. Whereas the lowering of the hematocrit (see FIG. 6) has a roughly comparable course with HES 130/0.5 and HES 200/0.5, the plasma viscosity (see FIG. 7) with the HES 130/0.5 compared to the HES 200/0.5 is significantly reduced in the temporal course.

EXAMPLE 3

Figure 8:
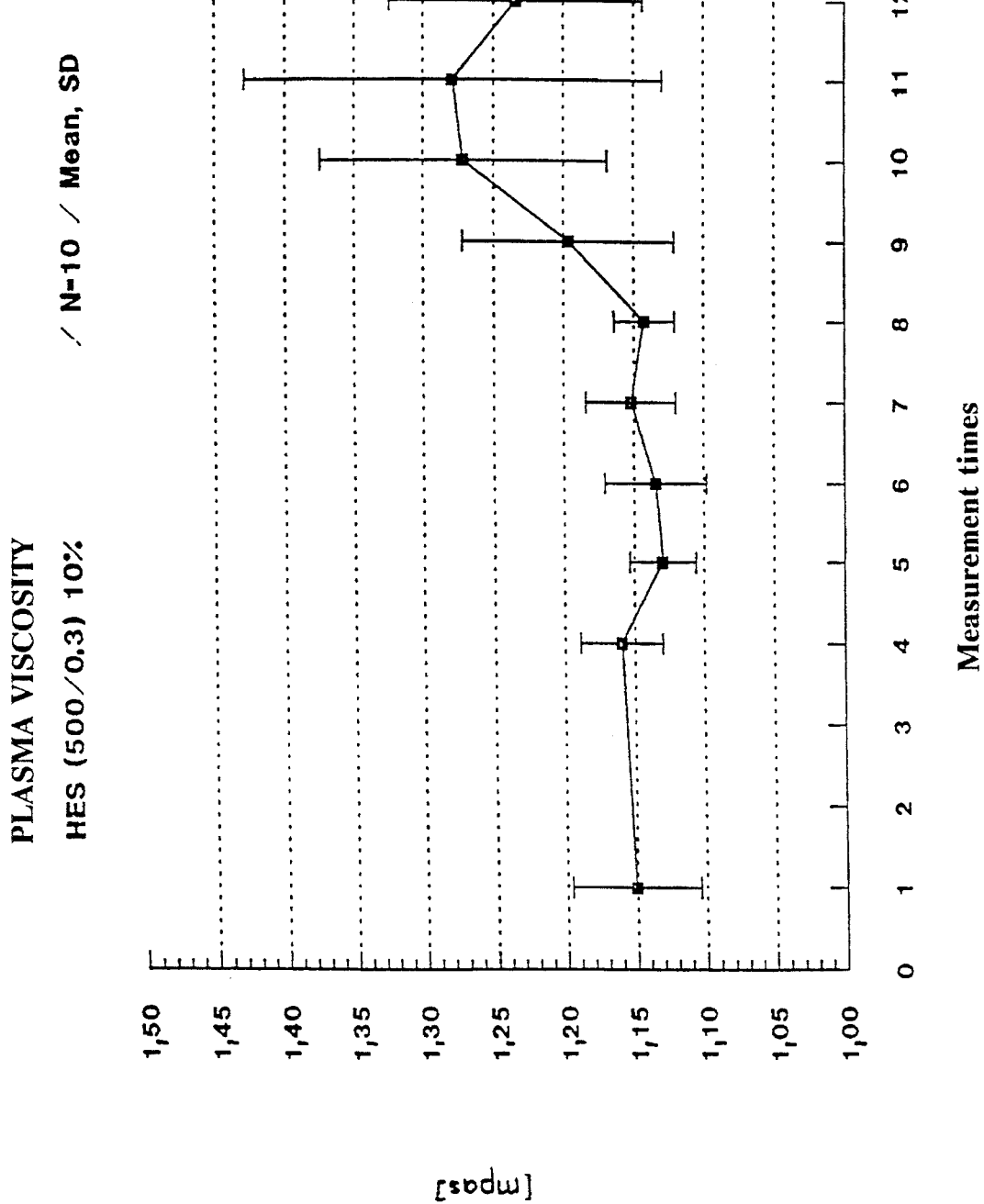
FIG. 8 shows changes in plasma viscosity following infusion of a 10 wt.-% solution of HES 500/0.

For comparison, the investigations described in Example 1 were repeated under the same conditions with the exception that instead of the 6 wt.-% solution of HES 130/0.5, a 10 wt.-% solution of HES 500/0.3 ($M_W$ 500,000, MS 0.28, and a $C_2/C_6$ ratio of 8.7) was infused. In the examination period of 72 hours, the change in plasma viscosity was measured at specific measurement times. The results obtained in these examinations can be seen in FIG. 8. The following table summarizes the changes in the plasma viscosity.

| Param. MT* | PLASMA VISCOSITY HES (500/0.3) 10% | | | | |
|---|---|---|---|---|---|
| | Mean | SD | Min | Max | N |
| Plasma viscosity 1 | 1.151 | 0.046 | 1.050 | 1.205 | 10 |
| Plasma viscosity 4 | 1.159 | 0.030 | 1.110 | 1.205 | 10 |
| Plasma viscosity 5 | 1.130 | 0.024 | 1.095 | 1.165 | 10 |
| Plasma viscosity 6 | 1.134 | 0.036 | 1.063 | 1.170 | 10 |
| Plasma viscosity 7 | 1.152 | 0.032 | 1.100 | 1.190 | 10 |
| Plasma viscosity 8 | 1.142 | 0.022 | 1.105 | 1.187 | 10 |
| Plasma viscosity 9 | 1.197 | 0.076 | 1.130 | 1.390 | 10 |
| Plasma viscosity 10 | 1.272 | 0.103 | 1.175 | 1.507 | 10 |
| Plasma viscosity 11 | 1.279 | 0.150 | 1.120 | 1.645 | 10 |
| Plasma viscosity 12 | 1.234 | 0.090 | 1.135 | 1.400 | 10 |

*Param. MT: Parameter--Name and Measurement Time
Test of temporal course according to FRIEDMANN***
[n.s.: $p > 0.05$*: $p \leq 0.05$: $p \leq 0.01$*: $p \leq 0.001$]

A comparison of the results with the course of the change in the plasma viscosity of HES 130/0.5 (see FIG. 2) shows a different course. With HES 500/0.3 as well, just as with HES 200/0.5, toward the end of the examination period, the plasma viscosity rises disadvantageously.

EXAMPLE 4

In another study 8 healthy male subjects were infused on 5 consecutive days in each case with 500 ml of a 6 wt.-% solution of HES 130/0.5 within 30 minutes. Over the examination period of 10 days, the serum HES concentration was determined at specific measurement times. The values obtained can be seen in FIG. 9.

FIG. 9 shows the course of the serum HES concentrations, which has a typical "sawtooth profile". The highest concentrations were measured at the end of the infusion; after an additional 6.5 hours (range to 1.6 mg/ml) as well as on the following morning the concentrations had already dropped significantly (range<0.8 mg/ml). The highest concentration measured, after the fifth infusion, was 4.73 mg/ml; however, already on the morning of the 6th day as well as on the following days, the concentration was <1.0 mg/ml. A statistical model which simulates a daily continuous infusion based on the present data calculated a maximum concentration after the end of infusion of 5.74 mg/ml.

The average molecular weight $M_W$ of the residual serum HES fractions, measured 7 hours after the beginning of the infusion and on days 6 through 10, respectively, was in the range from 70 through 80 kda, i.e., in the range of the renal threshold for hydroxyethyl starch.

What is claimed is:

1. A method for improving microcirculation in a patient, comprising:
   administering to the patient an effective amount of a hydroxyethyl starch having a molecular weight of about 110,000 to about 150,000, a substitution level MS of about 0.38 to about 0.5, a substitution level DS of about 0.32 to about 0.45, and a $C_2/C_6$ ratio from 8 to 20.

2. A method according to claim 1, for improving microcirculation in peripheral arterial occlusive disease in Stage II according to Fontaine.

3. A method according to claim 1, wherein the hydroxyethyl starch comprises a solution in the range of about 5 to about 15 wt-%.

4. A method according to claim 3, wherein the range is about 6 to about 10 wt-%.

* * * * *